(12) United States Patent
Cole

(10) Patent No.: US 11,202,662 B2
(45) Date of Patent: *Dec. 21, 2021

(54) PERCUTANEOUS FIXATOR AND METHOD OF INSERTION

(71) Applicant: J. Dean Cole, Orlando, FL (US)

(72) Inventor: J. Dean Cole, Orlando, FL (US)

(73) Assignee: J. Dean Cole, Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,170

(22) Filed: Aug. 15, 2019

(65) Prior Publication Data

US 2020/0054369 A1 Feb. 20, 2020

Related U.S. Application Data

(63) Continuation of application No. 14/954,809, filed on Nov. 30, 2015, now Pat. No. 10,383,666, which is a continuation of application No. 13/708,643, filed on Dec. 7, 2012, now Pat. No. 9,198,699, which is a continuation of application No. 12/343,243, filed on Dec. 23, 2008, now Pat. No. 8,328,805, which is a (Continued)

(51) Int. Cl.

| A61B 17/58 | (2006.01) |
|---|---|
| A61B 17/72 | (2006.01) |
| A61B 17/17 | (2006.01) |
| A61B 17/92 | (2006.01) |
| A61B 90/00 | (2016.01) |
| A61B 17/16 | (2006.01) |
| A61B 17/80 | (2006.01) |
| A61B 17/56 | (2006.01) |

(52) U.S. Cl.
CPC .............. *A61B 17/72* (2013.01); *A61B 17/16* (2013.01); *A61B 17/1703* (2013.01); *A61B 17/1725* (2013.01); *A61B 17/1735* (2013.01); *A61B 17/921* (2013.01); *A61B 90/00* (2016.02); *A61B 17/1764* (2013.01); *A61B 17/80* (2013.01); *A61B 2017/564* (2013.01)

(58) Field of Classification Search
CPC ... A61B 17/72; A61B 17/725; A61B 17/1764; A61B 17/1717; A61B 17/7225; A61B 17/921; A61B 17/7283
See application file for complete search history.

(56) References Cited

U.S. PATENT DOCUMENTS

| 4,781,181 A | 11/1988 | Tanguy |
| 5,100,404 A | 3/1992 | Hayes |

(Continued)

OTHER PUBLICATIONS

Campbell's Operative Orthopaedics (Seventh Edition), vol. Three, edited by A.H. Crenshaw, 1987, pp. 1634-1653.

(Continued)

*Primary Examiner* — Anu Ramana
(74) *Attorney, Agent, or Firm* — Haynes and Boone, LLP (57) ABSTRACT

The present invention provides a technique for percutaneous intramedullary fixation. A protective outer sheath is provided for internal fixation of the proximal tibia. Additionally, a unique intramedullary plate is provided that is adapted for percutaneous insertion into the intramedullary canal of a long bone. A plate holder is also provided that may be utilized through the outer sheath to drive and position a fixation plate within the intramedullary canal.

18 Claims, 5 Drawing Sheets

Related U.S. Application Data continuation of application No. 10/799,179, filed on Mar. 12, 2004, now Pat. No. 7,476,225.

(60) Provisional application No. 60/454,826, filed on Mar. 14, 2003.

(56) References Cited

U.S. PATENT DOCUMENTS

| | | | |
|---|---|---|---|
| 5,112,299 A | 5/1992 | Pascaloff | |
| 5,346,492 A | 9/1994 | Morgan | |
| 5,443,469 A | 8/1995 | Smith | |
| 5,624,447 A | 4/1997 | Myers | |
| 5,865,768 A | 2/1999 | Orr | |
| 5,951,561 A | 9/1999 | Pepper et al. | |
| 5,989,260 A | 11/1999 | Yao | |
| 6,036,696 A | 3/2000 | Lambrecht et al. | |
| 6,106,528 A | 8/2000 | Durham et al. | |
| 6,179,788 B1 | 1/2001 | Sullivan | |
| 6,270,499 B1 | 8/2001 | Leu et al. | |
| 6,354,989 B1 | 3/2002 | Nudeshima | |
| 6,419,678 B1 | 7/2002 | Asfora | |
| 6,488,684 B2 | 12/2002 | Bramlet et al. | |
| 6,656,189 B1 | 12/2003 | Wilson et al. | |
| 7,819,877 B2 | 10/2010 | Guzman et al. | |
| 2003/0004513 A1 | 1/2003 | Guzman et al. | |
| 2004/0153066 A1* | 8/2004 | Coon | A61B 17/155 606/54 |

OTHER PUBLICATIONS

Percutaneous intramedullary nailing of tibial shaft fractures: a new approach for prevention of anterior knee pain, A. H. Karladani, J. Styf, Injury, International Journal of Care of the Injured 32 (2001) 736-739.

* cited by examiner

PERCUTANEOUS FIXATOR AND METHOD OF INSERTION

CROSS REFERENCE

This application is a continuation of U.S. patent application Ser. No. 14/954,809, now U.S. Pat. No. 10,383,666, which is a continuation of U.S. patent application Ser. No. 13/708,643, now U.S. Pat. No. 9,198,699, which is a continuation of U.S. patent application Ser. No. 12/343,243, now U.S. Pat. No. 8,328,805, which is a continuation of U.S. patent application Ser. No. 10/799,179, now U.S. Pat. No. 7,476,225, which claims priority from U.S. Provisional patent application Ser. No. 60/454,826, filed on Mar. 14, 2003, and entitled "PERCUTANEOUS FIXATOR AND METHOD OF INSERTION," each of which is hereby incorporated by reference in its entirety.

BACKGROUND

The present invention relates to skeletal fixation. In one aspect, it provides improved instruments, fixation members and methods of insertion for tibial fixation utilizing an intra-articular insertion.

Tibial fixation utilizing elongated plates or rods disposed in the intramedullary canal or plating on the tibia cortex has been previously performed to provide fixation of the proximal tibia. In a traditional approach, a plate is placed on the periosteal cortex through an open or limited open surgical approach. Alternatively, the knee joint is flexed so that the surgeon can gain access to the proximal portion of the tibia intramedullary canal. In previous intramedullary approaches, the patella is moved laterally to provide direct access to the proximal portion of the tibia. This technique is known as a medial-patella tendon approach. In this procedure, much of the trauma associated with the surgical access to the proximal portion of the tibia occurs in moving the patella laterally and posteriorly because it blocks access to the desired entry site.

SUMMARY OF THE INVENTION

The present invention provides a method for percutaneous insertion of a fixation member for internal fixation from a supra-patella approach to the tibia. In one aspect of the invention, a protective sheath is positioned with a proximal portion positioned above (supra) the patella adjacent the femur and a distal end portion adjacent the proximal end of the tibia. In a preferred embodiment of the method of the present invention, an obturator is provided that is sized to be received within the protective sheath. The obturator is advanced from the supra patella access site to adjacent the tibia and the protective sheath is advanced over the obturator. In one aspect, a fixation member is joined to the proximal tibia after passing through the protective sheath. In a more preferred aspect, after gaining surgical access to the intramedullary canal of the tibia, a fixation member is advanced through the sheath and into the proximal portion of the intramedullary canal of the tibia. In a preferred aspect, screws or other fixation members are passed through the fixation member, such as a plate or a rod, to lock it and surrounding bone in a fixed position.

In another aspect of the present invention, a protective sheath is provided for percutaneous proximal tibial fixation. In one aspect, the sheath includes a distal end with a tapered tip. In another aspect, the distal end includes a radiopaque marker. More preferably, the tapered tip on the distal portion of the sheath is formed to substantially match the external geometry of the proximal tibia. In an alternative construction, the sheath may taper from a first diameter at its proximal end to a second smaller diameter at its distal end. Still further, the protective sheath may include a distal end adapted for fixedly engaging the bone of the tibia. In one preferred aspect, anchor pins are provided to engage the bone. In an alternative preferred aspect, the external surface of the distal end of the protective sheath includes external roughening including but not limited to, threads, ridges, knurling, teeth or grooves.

In yet another aspect of the present invention, a fixation plate is provided that is configured for passage through a sheath for percutaneous implantation. More specifically, in a preferred aspect, the plate includes an internal passage extending along its length adapted to receive a guiding member. In a preferred aspect, the channel is in substantial alignment with the longitudinal axis of the plate. In still a further preferred aspect of the present invention, the percutaneously inserted plate includes a proximal end adapted for engagement with an elongated insertion tool and a distal end configured for atraumatic insertion within the patient. In a more preferred embodiment, the distal end of the plate includes a first curvature along its width defining an insertion nose and a second curvature along its thickness presenting a rounded surface for engagement with the adjacent tissue.

In still a further aspect of the present invention, a kit is provided for percutaneous fixation member implantation. In a preferred aspect, the kit includes a protective sheath having an end for engagement with a long bone and an opposite free end. The kit further includes one or more fixation plates or rods adapted for sliding movement within the sheath. The kit may additionally include a fixation plate holder having a mechanism for releasably attaching to the plate and a length sufficient to position the fixation plate beyond the distal end of the sheath while at least a portion of the gripping tool extends beyond the free end of the sheath.

The present invention also provides a technique to permit percutaneous fixator insertion utilizing image-guided surgical techniques. More specifically, an obturator and/or a protective sheath may be provided with a reference marker identifiable by an image-guided surgery system. Additionally, in a preferred aspect a guide wire is also fitted within an image-guided sensor to denote its location within the bone of interest. In this technique, the plate gripping tool may also include a reference marker such that when the plate is fixably attached to the gripping tool, the reference marker denotes the location and orientation of the plate as registered by the image-guided surgical computers. In this manner, a surgeon may specifically identify the orientation of the guide wire and surrounding protective sheath to determine the trajectory of implantation. This may be determined through sequential x-ray imaging or other imaging techniques or by utilizing pre-defined images stored within a computer aided image-guided surgery system. After determination of the proper trajectory, a cutting tool or broach may be advanced within the guide sleeve and preferably guided by the guide wire to define an aperture extending into the intramedullary canal within the bone of interest. The cutting tool may then be withdrawn. A fixation plate may be gripped by an insertion tool and advance within the guide sheath to the predetermined position within the patient. It will be understood that the use of image-guided reference markers on the insertion tool may assist the surgeon in determining the orientation within the patient and the proper location extending along the bone. Additionally, the image-guided reference markers may assist the surgeon when placing nails through the bone and through the apertures in the fixation plate.

DETAILED DESCRIPTION OF THE PREFERRED EMBODIMENTS

Figures 1, 2A:
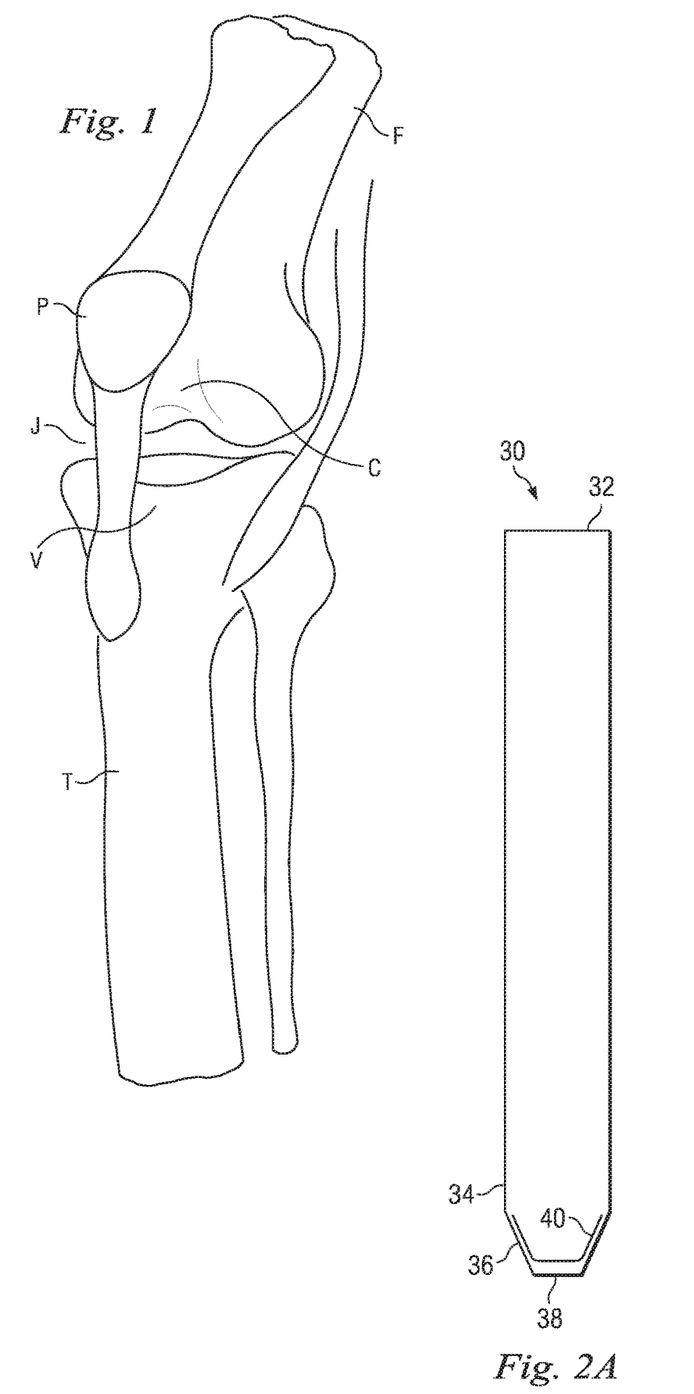
FIG. 1 is a perspective view of a human knee joint.
FIGS. 2A-2E illustrate a protective sheath in accordance with one aspect of the present invention.

The present invention provides improved techniques, instruments and internal fixation devices permitting percutaneous fixation within the intramedullary canal of the long bone. In a preferred aspect, the instrument technique and fixation devices may be utilized for plating of the proximal tibia. FIG. 1 illustrates a stylized human knee joint having a femur F joined to tibia T by patella P and the associated ligaments. Femur F includes a channel C through which the patella moves during flexion and extension of the knee joint. In a similar manner, tibia T includes a implantation site V at its proximal most portion. It would be understood, that the joint J normally includes cartilage to prevent or limit the contact between femur F and tibia T.

Figure 2B:
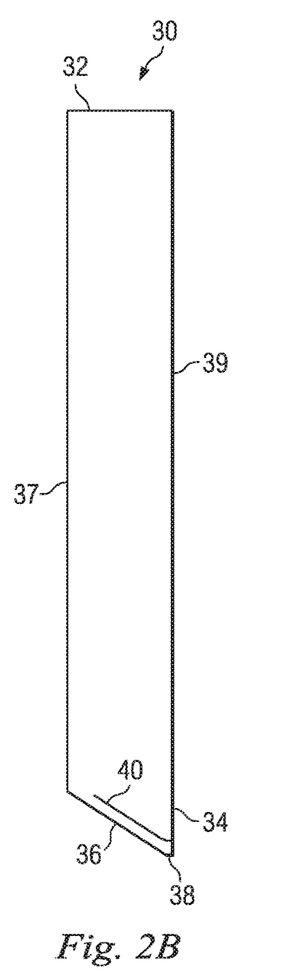
Figure 2C:
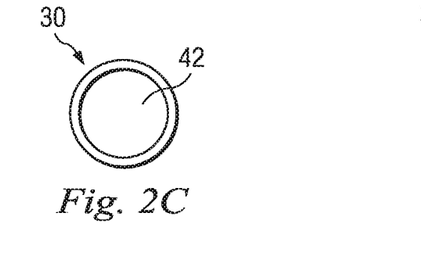
Figure 2D:
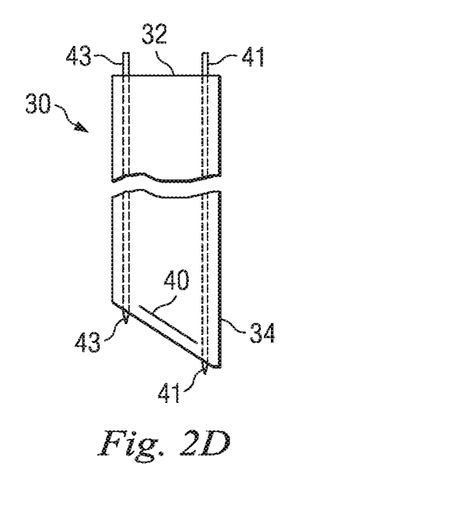
Figure 2E:
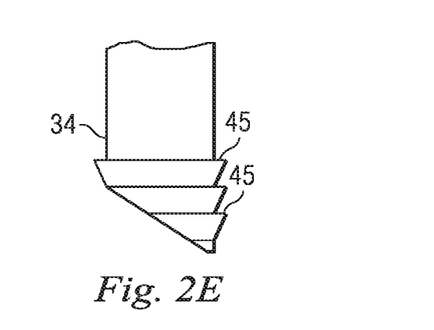

Referring now to FIGS. 2A through 2C, there is shown a protective sheath in accordance with one aspect of the present invention. Sheath 30 includes a proximal end 32 and an opposite distal end 34. Distal end 34 includes an extreme distal portion 38 having a blunt nose adapted to the engaged tissue in an atraumatic fashion. Tapered surface 36 extends from blunt nose 38 on long side wall 39 to short sidewall 37. Surface 36 and a similar surface on the opposite side may also assist the protective sheath 30 during insertion by mobilizing adjacent soft tissue to extend around the exterior of the guide sleeve rather than protrude within the internal passage 42. Additionally, distal end 34 is configured to substantially mimic and mate with the implantation site V of tibia T shown in FIG. 1. Distal portion 34 is also provided with a radiopaque marker 40. In a preferred aspect, protective sheath 30 is made from a radiolucent material such that x-ray or other imaging of the surrounding bone structures substantially unobstructed by its presence. Radiopaque marker 40 permits the user to determine where distal portion 34 is located within the patient and when it has been securely positioned against the proximal portion of the tibia. While the protective sheath of FIG. 2A is shown with substantially parallel side walls 37 and 39 extending from the proximal portion to the distal portion, it will be understood that the proximal portion 32 may have an opening defining a first diameter and the distal portion 34 may have an opening defining a second diameter, wherein the first diameter is substantially larger than the second diameter. In another preferred aspect, the change from the first large diameter to the second smaller diameter may extend along the length in a substantially continuous manner to define a tapering protective sheath. As shown in FIG. 2D, anchoring pins 41 and 43 may extend along the length of the sheath 30. The distal ends of the pins may be withdrawn into the tube during sheath insertion and extended into the bone when the sheath is properly positioned. FIG. 2E illustrates a series of externally projecting ridges 45 that may ease insertion of the sheath into the patient but inhibit removal of the sheath from surrounding bone or soft tissue.

Figure 3A:
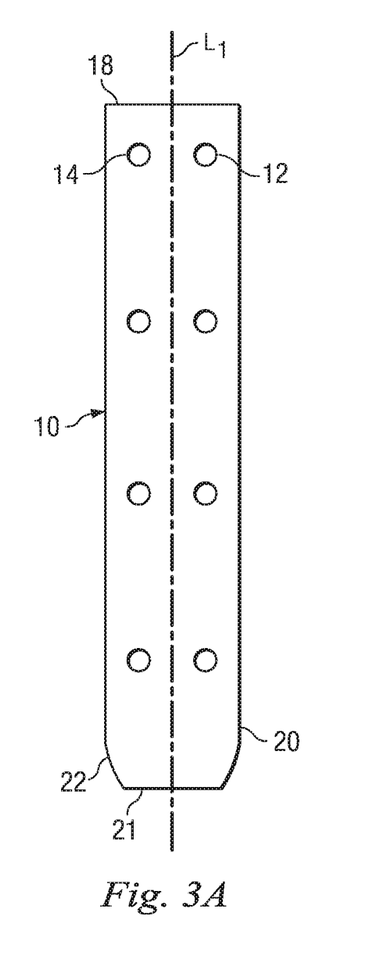
FIGS. 3A-3C illustrate an intramedullary fixation member in accordance with another aspect of the present invention.
Figure 3B:
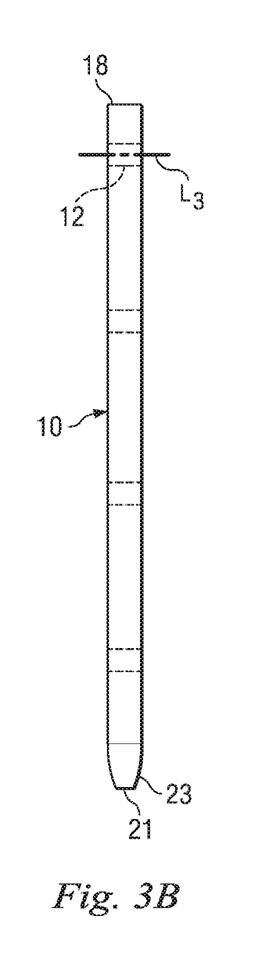
Figure 3C:
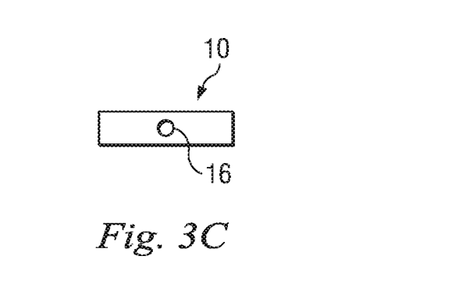

Referring now to FIGS. 3A through 3C, there is shown an intramedullary fixation member in accordance with another aspect of the present invention. Fixation plate 10 has a proximal end 18 and a distal portion 20. Distal portion 20 includes a leading tip 21 and a lateral transition 22 that extends from leading tip 21 to the main body of plate 30 transitioning the width of the plate adjacent the leading tip in a continuous manner to the full width of the main body of plate 10. In one preferred aspect, the plate has a width of approximately 8 to 16 mm. Additionally, as shown in FIG. 3B, in the side view, it is apparent that the preferred aspect thickness transition area 23 extends from leading tip 21 to the main body of plate 10 such that the thickness of the plate increases from the leading tip in a substantially continuous manner until it approximates the width of the main body of plate 10. Plate 10 includes a plurality of fixation apertures along its length such as those shown at reference numbers 12 and 14. It will be appreciated that the placement and orientation of the screw apertures may be dependent upon the particular medical indication. More specifically, in the illustrated embodiment the longitudinal axis $L_1$ of plate 10 is substantially perpendicular to the longitudinal axis of $L_3$ of fixation aperture 12. However, it will be appreciated that in many applications the longitudinal axis $L_3$ may be set at a specific angle with respect to longitudinal axis $L_1$ such that the fixation screw or other fixation number extends at a non-perpendicular orientation with respect to plate 10.

Referring now to FIG. 3C, plate 10 includes a longitudinal bore 16 extending along substantially its entire length. As will be illustrated and described further herein, bore 16 is sized to receive a guide wire member along its length. While an internal bore 16 is shown that extends along the substantial length of plate 10, it will be appreciated that a similar guiding feature may be implemented utilizing a fixture external to the plate such that it can guide along a guide member during the implantation process.

Figure 4:
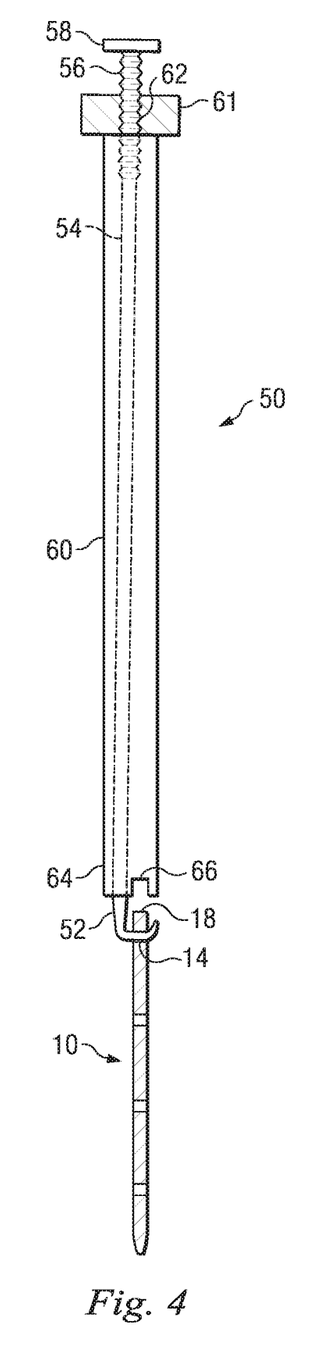
FIG. 4 illustrates a fixation plate gripping tool.
Figure 5:
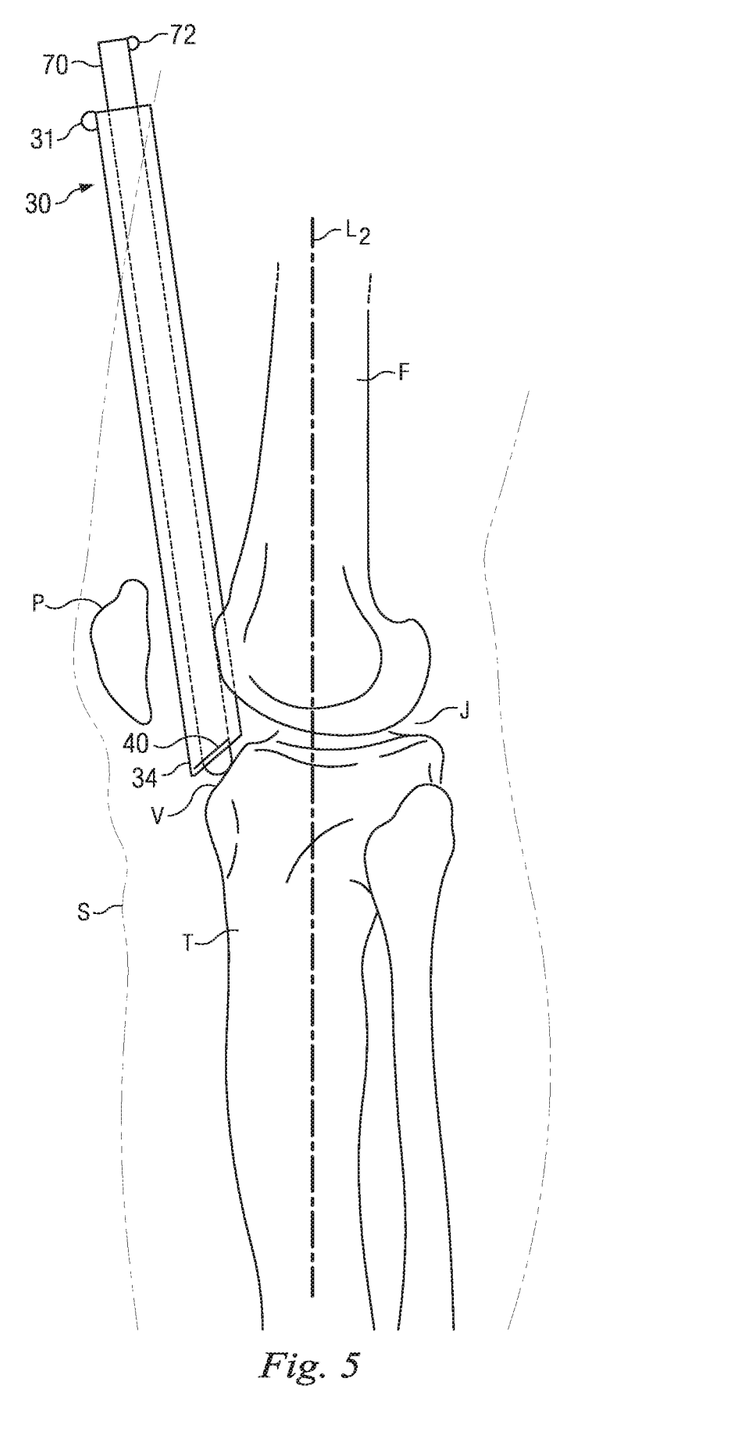
FIG. 5 is a stylized side view of a human knee joint showing the supra patella insertion of a protective sheath according to the present invention.

Referring now to FIG. 4, there is shown a percutaneous surgical tool adapted for implantation of an intramedullary plate. Plate holder 50 includes an inner shaft 54 having a hook 52 at its distal end. Inner shaft 54 includes a series of external threads 56 disposed adjacent the proximal end. Additionally, a handle 58 is provided at the proximal end to facilitate rotation of the plate holder 50. While a handle is shown for the purpose of illustration, it will be appreciated that an internal or external driving pattern may be provided at the proximal end of internal shaft 54 such that a tool may be engage the shaft to facilitate rotation. Inner shaft 54 is disposed within outer tube 60. Outer tube 60 has a ring 61 pivotally mounted on its proximal end. Ring 61 includes a series of internal threads 62 configured and adapted for threaded engagement with external threads 56. A portion of plate 10 is shown in cross section with hook 52 extending through fixation aperture 14. The distal end 64 of plate holder 50 includes a socket 66 adapted and configured to substantially mate with proximal end 18 of plate 10. It will be appreciated that as ring 61 is rotated with respect to inner shaft 54 to retract the distal portion into the outer tube 60, hook 52 will cause proximal end 18 to positively seat within socket 66. In a prepared aspect, it is intended that the engagement between socket 66 and proximal end 18 will permit substantial force to be applied along plate holder 50 both urging the plate forward along the longitudinal axis of the plate and permitting the adjustment of the rotational orientation of the plate about its longitudinal axis. Further, a separate aperture, recess or other structure may be provided on the plate to mate with an alternative plate holder Referring now to FIG. 5, there is shown a stylized human knee joint with a femur F, tibia T, patella P and the intervening joint J. In a preferred aspect of the invention, an obturator 70 is inserted through the patient's skin S above the patella P, in a supra-patella fashion. The obturator extends along the femur F under the patella P across the joint J and to the proximal portion of the tibia. As can be seen in FIG. 5, femur F and tibia T are in substantial alignment as the patient's leg is in the fully extended position. Thus, it is clear that the patient's bones are in a properly aligned position and in subsequent steps bone portions may be fixed to maintain that position during the healing process. Additionally, in this extended position, the patella tendons are relatively relaxed permitting atraumatic movement of the patella laterally and/or anteriorly. X-rays or other images may be taken to demonstration that obturator 70 is properly aligned within the patient's bone. Protective sheath 30 may then be advanced over guide wire 70 through the patient's skin along the femur and into the joint area J. Alternatively, the obturator and sheath may be advanced into the patient as a unit. The obturator may include a central bore for receiving a guide member 69. Preferably, the obturator will match the internal diameter of the sheath 30 to facilitate proper positioning and prevent tissue from entering the internal bore 42. The obturator may be withdrawn after the sheath is positioned. It will be appreciated that at this point or prior to placing the guide member, a surgeon may evaluate the contents of the joint space through the sheath 30 and evacuate any debris or damaged tissue prior to further surgical steps.

The distal end 34 of protective sheath 30 may be advanced until it is in substantial alignment and/or engagement with the proximal end of tibia T. In preferred aspects, the distal end 34 is configured to substantially mate with the implantation site V defined in the outer surface of the proximal tibia. Further imaging may be utilized to show that radiopaque marker 40 is aligned in the proper position with respect to the adjacent bony structures. In one aspect of the procedure, the outer surface of protective sheath 30 may lie within at least a portion of channel C of femur F. Additionally, obturator 70 may include a reference marker 72 that may be utilized by an image-guided surgery system to provide a reference for the surgeon in its placement and later use. Additionally, outer sheath 30 may also include a reference marker 31 that may be utilized with an image-guided surgery system for alignment orientation within the patient.

Figure 6:
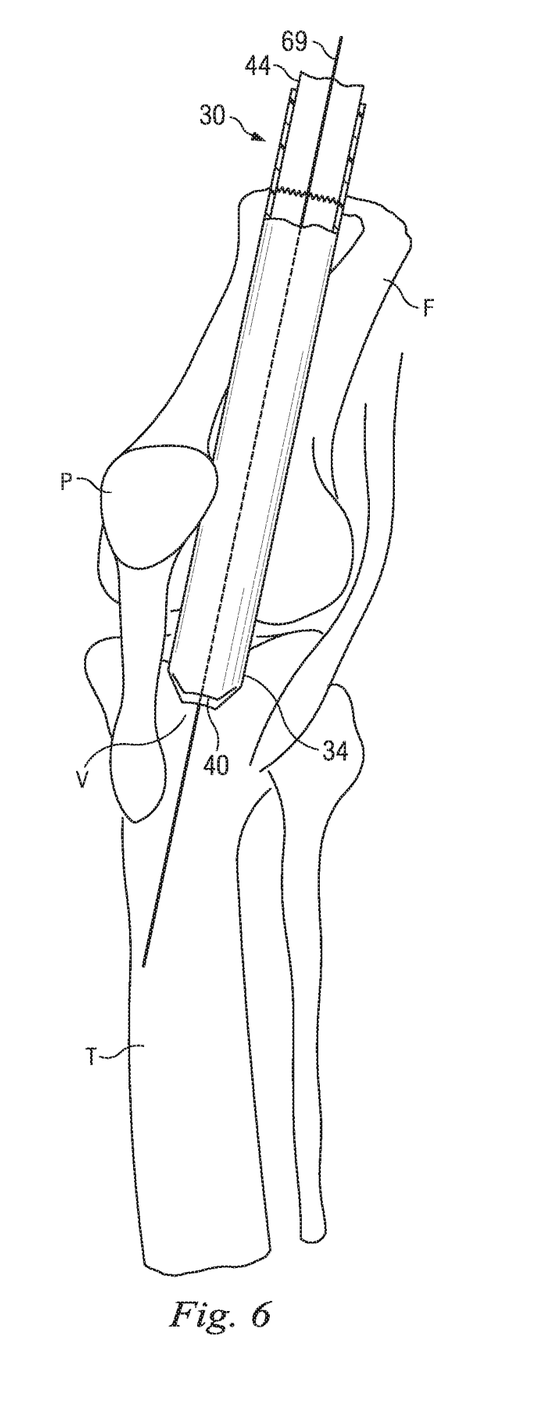
FIG. 6 is a perspective view of the protective sheath associated with the knee joint of FIG. 1.

Turning now to FIG. 6, there is shown a human knee joint in a partial cross sectional perspective view with the outer sheath 30 positioned within the implantation site V of the proximal tibia. As shown in FIG. 6, radiopaque marker 40 is in substantial alignment with the adjacent bony structure of the implantation site V. Thus, it is anticipated that distal end 34 will be in substantial engagement with a portion of the proximal tibia. Outer sheath 30 extends from an entry point above the patella along the femur and under the patella to engagement with a proximal portion of the tibia. If desired, a fixation plate may be passed through sheath 30 for placement on the periosteal cortex of the proximal tibia. Alternatively, a guide wire 69 may be positioned through sheath 30 into the intramedullary canal of the proximal tibia. A cutting instrument 44 such as a broach or awl may be advanced along guide wire 69 to form an aperture through the proximal tibia and into the intramedullary canal. Sheath 30 may be utilized to provide a channel for evacuation of debris from the cutting site and to inhibit debris from entering the knee joint. In one technique, a hole is formed in the proximal tibia approximating the diameter of sheath 30. The distal end 34 such as shown in FIG. 2E may be advanced into the hole to firmly engage the sheath 30 to the surrounding bone. In an alternative procedure, the embodiment of protective sheath 30 shown in FIG. 2D may be utilized. In this procedure, imaging may be utilized to verify that radiopaque marker 40 is in the proper position. Anchor pins 41 and 43 may then be advanced distally to extend into the bone and affirmatively engage the outer sheath 30 to the proximal portion of the tibia T.

Figure 7:
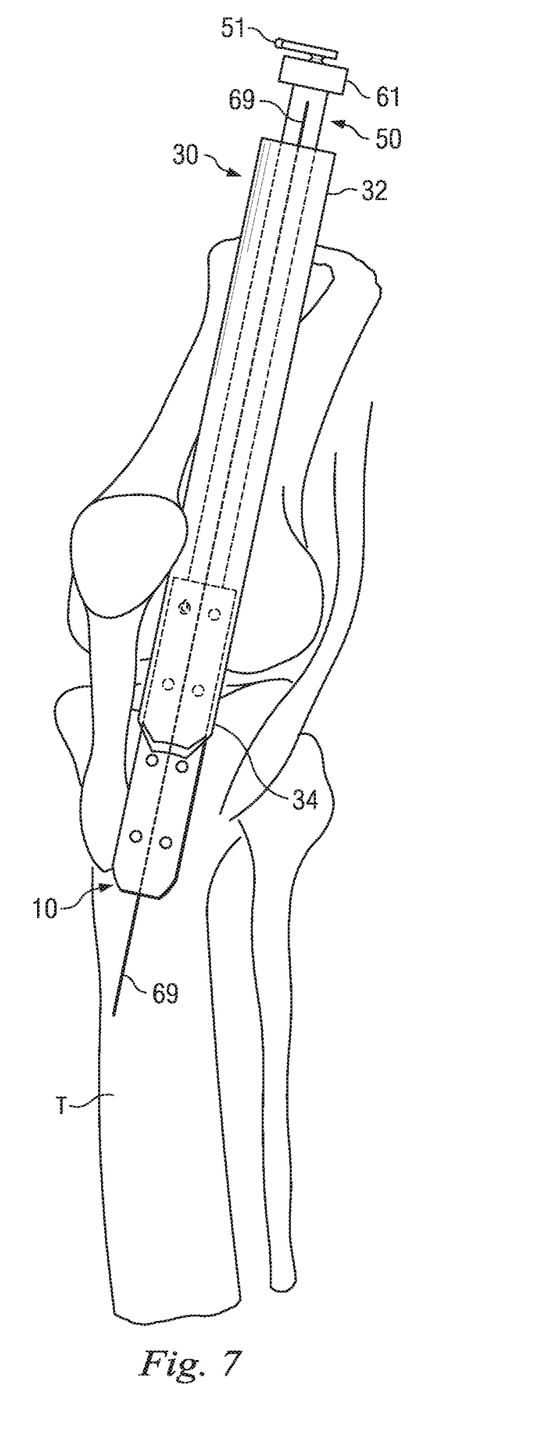
FIG. 7 is a perspective view of a knee joint during insertion of an intramedullary fixation plate in accordance with the present invention.

Referring now to FIG. 7, intramedullary fixation plate 10 is advanced through outer sheath 30 into the proximal portion of tibia T. In a preferred aspect, guide wire 69 is inserted into bore 16 extending along the longitudinal axis of plate 10 to guide the plate into position. Plate 10 is grasped by plate holder 50 and is advanced along guide wire 69 in the proximal tibia. It will be appreciated that plate holder 50 may be rotated to adjust the rotational orientation of plate 10 within outer sheath 30. Additionally, force may be applied to plate holder 50 to adjust the longitudinal and rotational position of plate 10 within the intramedullary canal. Plate holder 50 may be fitted with a reference marker 51 to permit an image-guided surgery system to approximate the longitudinal and rotational position of fixation plate 10. Although not necessarily drawn to scale in FIG. 7, it will be understood that plate holder 50 has a length that is substantially longer than the length of protective sheath 30 such that plate 10 may be fully positioned within the intramedullary canal of the proximal tibia and extended beyond the distal portion 34 of sheath 30 with a substantial portion of plate holder 50 extending beyond proximal portion 32. If necessary, impaction force may be applied to plate holder 50 to drive fixation plate 10 into position. Once fixation plate 10 has been properly positioned within the intramedullary canal of the proximal tibia, ring 61 may be rotated with respect to outer tube 60 to thereby release hook 52 from plate 10. After the plate holder 50 is disengaged from the plate 10, it may be withdrawn from outer sheath 30. Although a plate has been shown for the purpose of illustration, an intramedullary rod may also be implanted utilizing the procedures described above.

Figure 8:
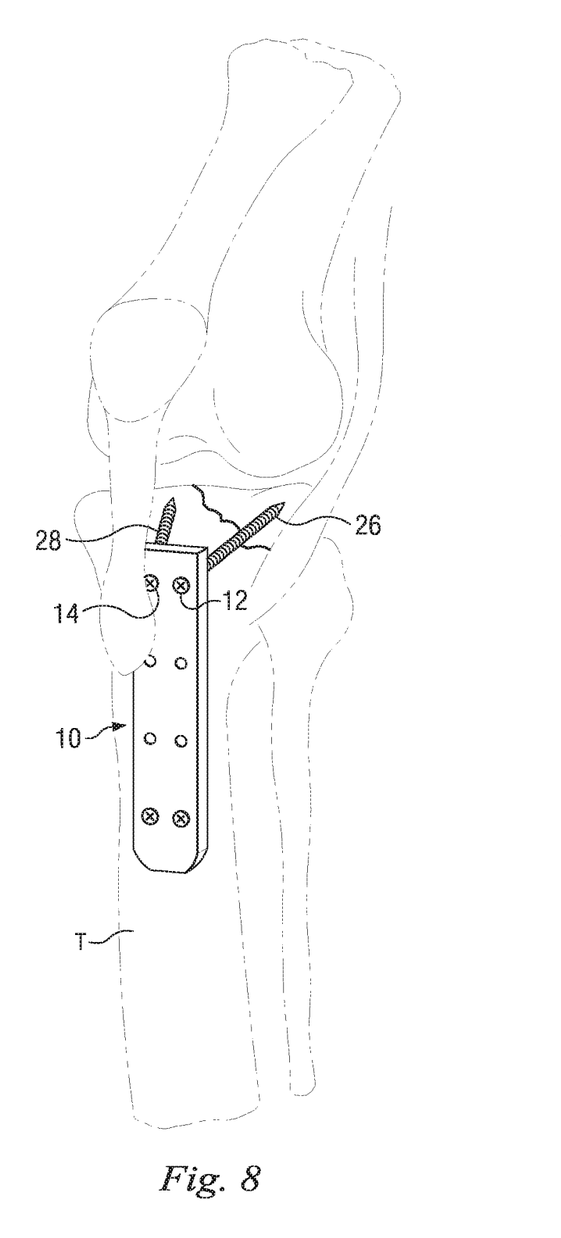
FIG. 8 is a perspective view showing the intramedullary fixation plate implanted within the intramedullary canal of a human tibia and associated fixation screws.
Figure 9:
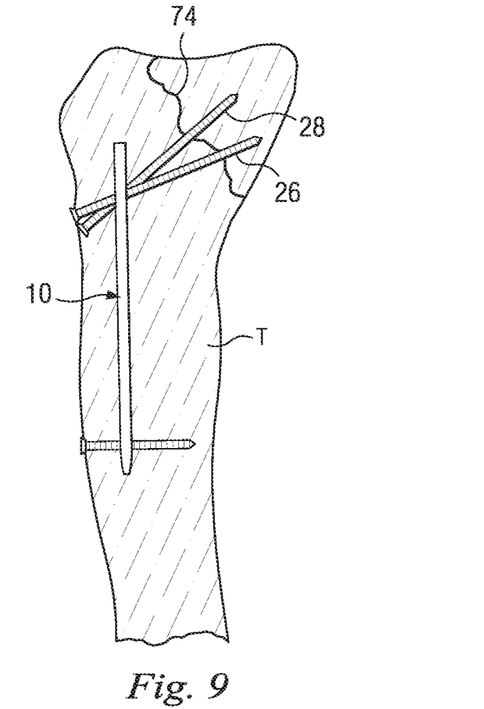
FIG. 9 is a partial cross-sectional view of the tibia of FIG. 8.

Referring now to FIG. 8, fixation members 26 and 28 may be positioned through fixation apertures 12 and 14 to fixedly connect the intramedullary plate to surrounding bone. It will be appreciated that the placement of fixation members 26 and 28 may be performed with the plate holder attached to assist in the alignment of the screw guides with the fixation apertures 12 and 14, respectively. A mechanical guide may be utilized that is joined to plate holder 50 to assist in the placement of the fixation members. Alternatively or in combination, image-guided surgery may be utilized with reference marker 51 to provide the surgeon aiming guidance for positioning the fixation member directly through the aperture of the fixation plate. Any number of screws or other fixation members may be positioned through plate 10 as required for the surgical procedure. Additionally, as best seen in FIG. 9, fixation members 26 and 28 may extend at non perpendicular angles through the fixation apertures of plate 10. In the embodiment illustrated in FIG. 9, a fractured 74 is illustrated in the proximal tibia and fixation members 26 and 28 extend across the fraction into the distal bone thereby fixing the proximal bone and distal portion to the intramedullary plate. Although not shown, a separate locking mechanism may be provided with the plate to positively lock the fixation members to the plate. Once the appropriate fixation members have been implanted, the protective sheath 30 and guide wire 69 may be removed from the patient and the percutaneous puncture wound may be closed.

The foregoing description of the preferred embodiments of the present invention is intended to provide a teaching to those skilled in the art. The description is provided without limitation as to alternative features and components that come within the scope of the invention.

What is claimed is:

1. A method for suprapatellar insertion of a tibial fixation member, the method comprising:
    creating a surgical access site that extends above a patella;
    moving a sheath through the surgical access site such that:
        the sheath extends proximate to a femur and the patella; and
        a distal portion of the sheath is proximate to a proximal portion of a tibia;
    forming, using a first instrument advanced through the sheath, an aperture in the proximal portion of the tibia such that the aperture extends into an intramedullary canal; and
    inserting the tibial fixation member into the intramedullary canal.

2. The method of claim 1, wherein the sheath extends under the patella.

3. The method of claim 1, wherein the sheath extends between the patella and the femur.

4. The method of claim 1, wherein the sheath extends along the femur.

5. The method of claim 1, wherein the sheath extends within a channel of the femur.

6. The method of claim 1, wherein the first instrument comprises a broach or an awl.

7. The method of claim 1, further comprising moving a second instrument through the surgical access site.

8. The method of claim 7, wherein the second instrument comprises an obturator.

9. The method of claim 7, wherein the sheath and the second instrument are moved separately.

10. The method of claim 7, wherein the sheath and the second instrument are moved as a unit.

11. The method of claim 1, further comprising:
    atraumatically moving the patella.

12. The method of claim 1, further comprising:
    positioning a guide member through the sheath.

13. The method of claim 12, further comprising:
    advancing the first instrument along the guide member.

14. The method of claim 1, wherein inserting the tibial fixation member includes advancing the tibial fixation member through the sheath.

15. The method of claim 1, further comprising:
    anchoring the tibial fixation member to the tibia with a plurality of bone engagement members.

16. The method of claim 15, wherein the plurality of bone engagement members comprises a plurality of screws sized and shaped for engagement with the tibia through apertures of the fixation member.

17. The method of claim 1, wherein moving the sheath is performed while the femur and the tibia are aligned with a leg of a patient fully extended.

18. The method of claim 1, wherein the sheath is substantially tubular.

* * * * *